US 6,640,050 B2

(12) United States Patent
Nichols et al.

(10) Patent No.: US 6,640,050 B2
(45) Date of Patent: Oct. 28, 2003

(54) FLUID VAPORIZING DEVICE HAVING CONTROLLED TEMPERATURE PROFILE HEATER/CAPILLARY TUBE

(75) Inventors: Walter A. Nichols, Chesterfield, VA (US); Kenneth A. Cox, Midlothian, VA (US); Douglas D. McRae, Chesterfield, VA (US); Tung Tien Nguyen, Midlothian, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 0 days.

(21) Appl. No.: 09/957,026

(22) Filed: Sep. 21, 2001

(65) Prior Publication Data

US 2003/0056791 A1 Mar. 27, 2003

(51) Int. Cl.$^7$ .............................. F24F 6/00; F22B 29/06
(52) U.S. Cl. .................................. 392/390; 392/397
(58) Field of Search .................. 392/311, 312, 392/313, 314, 319, 320, 321, 386, 387, 394, 396, 397; 128/203.17, 203.26, 203.27; 219/540, 541; 338/327, 328, 330

(56) References Cited

U.S. PATENT DOCUMENTS

| 2,896,856 A | 7/1959 | Kravits |
| 3,084,698 A | 4/1963 | Smith |
| 3,157,179 A | 11/1964 | Paullus et al. |

(List continued on next page.)

FOREIGN PATENT DOCUMENTS

| BE | 354004 A | 9/1928 |
| BE | 354094 A | 9/1928 |
| DE | 1036470 B1 | 8/1958 |

(List continued on next page.)

OTHER PUBLICATIONS

Barry, P.W. et al. "In Vitro Comparison of the Amount of Salbutamol Available for Inhalation From Different Formulations Used with Different Spacer Devices" Eur Respir J 1997; 10:1345–1348.

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994 (023).

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp 97–102.

(List continued on next page.)

*Primary Examiner*—Sang Paik
(74) *Attorney, Agent, or Firm*—Burns, Doane, Swecker & Mathis, LLP

(57) ABSTRACT

A fluid vaporizing device useful for vaporizing fluid into an aerosol includes a capillary tube made from an electrically conductive material, an upstream electrode connected to the tube, and a downstream electrode connected to the tube and provided with an electrical resistivity sufficient to cause heating of the downstream electrode during operation to approximately the same temperature as the tube at the point of connection. The upstream and downstream electrodes connected to the capillary tube divide the tube into an initial feed section, a heated section, and a tip. A source of material to be volatilized is provided to the tube at the feed section, passes downstream into the heated section, is vaporized, and then exits from the tube through the tip. The temperature profile of the tube along the heated section is controlled by varying parameters to substantially eliminate any effect of the downstream electrode as a heat sink. These parameters may include the electrical resistivity of the downstream electrode, its cross-sectional area, and its length.

14 Claims, 2 Drawing Sheets

U.S. PATENT DOCUMENTS

| | | |
|---|---|---|
| 3,162,324 A | 12/1964 | Houser |
| 3,431,393 A | 3/1969 | Katsuda |
| 3,486,663 A | 12/1969 | Humphrey |
| 3,658,059 A | 4/1972 | Steil |
| 3,716,416 A | 2/1973 | Adlhart et al. |
| 3,750,961 A | 8/1973 | Franz |
| 3,847,304 A | 11/1974 | Cohen |
| 3,859,398 A | 1/1975 | Havstad |
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |
| 3,987,941 A | 10/1976 | Blessing |
| 3,993,246 A | 11/1976 | Erb et al. |
| 3,995,371 A | 12/1976 | O'Keefe |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,259,409 A | 3/1981 | Arnold |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,575,609 A | 3/1986 | Fassel et al. |
| 4,627,432 A | 12/1986 | Newell et al. |
| 4,649,911 A | 3/1987 | Knight et al. |
| 4,682,010 A | 7/1987 | Drapeau et al. |
| 4,695,625 A | 9/1987 | Macdonald |
| 4,700,657 A | 10/1987 | Butland |
| 4,730,111 A | 3/1988 | Vestal et al. |
| 4,735,217 A | 4/1988 | Gerth et al. |
| 4,744,932 A | 5/1988 | Browne |
| 4,749,778 A | 6/1988 | Fukuzawa et al. |
| 4,762,995 A | 8/1988 | Browner et al. |
| 4,764,660 A * | 8/1988 | Swiatosz .................... 392/397 |
| 4,776,515 A | 10/1988 | Michalchik |
| 4,790,305 A | 12/1988 | Zoltan et al. |
| 4,811,731 A | 3/1989 | Newell et al. |
| 4,819,625 A | 4/1989 | Howe |
| 4,819,834 A | 4/1989 | Thiel |
| 4,829,996 A | 5/1989 | Noakes et al. |
| 4,837,260 A | 6/1989 | Sato et al. |
| 4,848,374 A | 7/1989 | Chard et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,922,901 A | 5/1990 | Brooks et al. |
| 4,926,852 A | 5/1990 | Zoltan et al. |
| 4,935,624 A | 6/1990 | Henion et al. |
| 4,941,483 A | 7/1990 | Ridings et al. |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldron |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,096,092 A | 3/1992 | Devine |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Müller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,217,004 A | 6/1993 | Blasnik et al. |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,290,540 A | 3/1994 | Prince et al. |
| 5,298,744 A | 3/1994 | Mimura et al. |
| 5,299,565 A | 4/1994 | Brown |
| 5,322,057 A | 6/1994 | Raabe et al. |
| 5,327,915 A | 7/1994 | Porenski et al. |
| 5,342,180 A | 8/1994 | Daoud |
| 5,342,645 A | 8/1994 | Eisele et al. |
| 5,349,946 A | 9/1994 | McComb |
| 5,395,445 A | 3/1995 | Bohanan |
| 5,421,489 A | 6/1995 | Holzner, Sr. et al. |
| 5,462,597 A | 10/1995 | Jubran |
| 5,474,059 A | 12/1995 | Cooper |
| 5,509,557 A | 4/1996 | Jimarez et al. |
| 5,515,842 A | 5/1996 | Ramseyer et al. |
| 5,522,385 A | 6/1996 | Lloyd et al. |
| 5,556,964 A | 9/1996 | Hofstraat et al. |
| 5,559,923 A * | 9/1996 | Robelen .................... 392/397 |
| 5,564,442 A | 10/1996 | MacDonald et al. |
| 5,565,677 A | 10/1996 | Wexler |
| 5,575,929 A | 11/1996 | Yu et al. |
| 5,585,045 A | 12/1996 | Heinonen et al. |
| 5,617,844 A | 4/1997 | King |
| 5,642,728 A | 7/1997 | Andersson et al. |
| 5,674,860 A | 10/1997 | Carling et al. |
| 5,682,874 A | 11/1997 | Grabenkort et al. |
| 5,706,389 A * | 1/1998 | Pohler .................... 392/397 |
| 5,730,158 A | 3/1998 | Collins et al. |
| 5,743,251 A | 4/1998 | Howell et al. |
| 5,756,995 A | 5/1998 | Maswadeh et al. |
| 5,765,724 A | 6/1998 | Amberg et al. |
| 5,823,178 A | 10/1998 | Lloyd et al. |
| 5,839,430 A | 11/1998 | Cama |
| 5,855,202 A | 1/1999 | Andrade |
| 5,856,671 A | 1/1999 | Henion et al. |
| 5,863,652 A | 1/1999 | Matsumura et al. |
| 5,869,133 A | 2/1999 | Anthony et al. |
| 5,870,524 A * | 2/1999 | Swiatosz .................... 392/394 |
| 5,872,010 A | 2/1999 | Karger et al. |
| 5,878,752 A | 3/1999 | Adams et al. |
| 5,881,714 A | 3/1999 | Yokoi et al. |
| 5,906,202 A | 5/1999 | Schuster et al. |
| 5,914,122 A | 6/1999 | Otterbeck et al. |
| 5,932,249 A | 8/1999 | Gruber et al. |
| 5,932,315 A | 8/1999 | Lum et al. |
| 5,934,272 A | 8/1999 | Lloyd et al. |
| 5,934,273 A | 8/1999 | Andersson et al. |
| 5,944,025 A | 8/1999 | Cook et al. |
| 5,954,979 A | 9/1999 | Counts et al. |
| 5,957,124 A | 9/1999 | Lloyd et al. |
| 5,970,973 A | 10/1999 | Gonda et al. |
| 5,970,974 A | 10/1999 | Van Der Linden et al. |
| 5,978,548 A | 11/1999 | Holmstrand et al. |
| 5,993,633 A | 11/1999 | Smith et al. |
| 6,014,970 A | 1/2000 | Ivri et al. |
| 6,053,176 A | 4/2000 | Adams et al. |

| | | |
|---|---|---|
| 6,054,032 A | 4/2000 | Haddad et al. |
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,071,554 A | 6/2000 | Isomura et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañnán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,453 B1 * | 2/2001 | Lin .......................... 102/334 |
| 6,189,803 B1 | 2/2001 | Gañán-Calvo |
| 6,192,882 B1 | 2/2001 | Gonda |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 2001/0032647 A1 | 10/2001 | Schuster et al. |

FOREIGN PATENT DOCUMENTS

| | | |
|---|---|---|
| EP | 0358114 A | 3/1990 |
| EP | 0642802 A2 | 5/1996 |
| FR | 667979 A | 10/1929 |
| HU | 216121 B | 3/1991 |
| HU | 207457 A | 4/1993 |
| HU | P953409 | 6/1994 |
| HU | 168128 B | 11/1997 |
| WO | 94/09842 A | 5/1994 |
| WO | 98/17131 | 4/1998 |

OTHER PUBLICATIONS

Hou, Shuguang et al. *Solution Stability of Budensonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994) (023).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]"Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 766–770, Jul. 1980.

Notification of Transmittal of the International Search Report or the Declaration dated Feb. 14, 2003 for PCT/US02/28703.

Written Opinion for PCT/US02/28703 dated Jul. 8, 2003.

* cited by examiner

FLUID VAPORIZING DEVICE HAVING CONTROLLED TEMPERATURE PROFILE HEATER/CAPILLARY TUBE

BACKGROUND OF THE INVENTION

1. Field of the Invention

The present invention relates generally to fluid vaporizing devices such as aerosol generators.

2. Brief Description of the Related Art

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms, distributing insecticides and delivering paint and lubricant.

Various techniques are known for generating aerosols. For example, U.S. Pat. Nos. 4,811,731 and 4,627,432 disclose devices for administering medicaments to patients in which a capsule is pierced by a pin to release a medicament in powder form. A user then inhales the released medicament through an opening in the device. While such devices may be acceptable for use in delivering medicaments in powder form, they are not suited to delivering medicaments in liquid form. The devices are also, of course, not well-suited to delivery of medicaments to persons who might have difficulty in generating a sufficient flow of air through the device to properly inhale the medicaments, such as asthma sufferers. The devices are also not suited for delivery of materials in applications other than medicament delivery.

Another well-known technique for generating an aerosol involves the use of a manually operated pump which draws liquid from a reservoir and forces it through a small nozzle opening to form a fine spray. A disadvantage of such aerosol generators, at least in medicament delivery applications, is the difficulty of properly synchronizing inhalation with pumping. More importantly, however, because such aerosol generators tend to produce particles of large size, their use as inhalers is compromised because large particles tend to not penetrate deep into the lungs.

One of the more popular techniques for generating an aerosol including liquid or powder particles involves the use of a compressed propellant, often containing a chloro-fluoro-carbon (CFC) or methylchloroform, to entrain a material, usually by the Venturi principle. For example, inhalers containing compressed propellants such as compressed gas for entraining a medicament are often operated by depressing a button to release a short charge of the compressed propellant. The propellant entrains the medicament as the propellant flows over a reservoir of the medicament so that the propellant and the medicament can be inhaled by the user.

In propellant-based arrangements, however, a medicament may not be properly delivered to the patient's lungs when it is necessary for the user to time the depression of an actuator such as a button with inhalation. Moreover, aerosols generated by propellant-based arrangements may have particles that are too large to ensure efficient and consistent deep lung penetration. Although propellant-based aerosol generators have wide application for uses such as antiperspirant and deodorant sprays and spray paint, their use is often limited because of the well-known adverse environmental effects of CFC's and methylchloroform, which are among the most popular propellants used in aerosol generators of this type.

In drug delivery applications, it is typically desirable to provide an aerosol having average mass median particle diameters of less than 2 microns to facilitate deep lung penetration. Propellant based aerosol generators are incapable of generating aerosols having average mass median particle diameters less than 2 microns. It is also desirable, in certain drug delivery applications, to deliver medicaments at high flow rates, e.g., above 1 milligram per second. Some aerosol generators suited for drug delivery are incapable of delivering such high flow rates in the 0.2 to 2.0 micron size range.

Commonly owned U.S. Pat. Nos. 5,743,251 and 6,234,167, which are hereby incorporated by reference in their entireties, disclose aerosol generators, along with certain principles of operation and materials used in an aerosol generator, as well as methods of producing an aerosol, and an aerosol.

SUMMARY OF THE INVENTION

The invention provides a fluid vaporizing device that includes a capillary tube made from an electrically conductive material, with the capillary tube providing a passageway for a fluid. At least two electrodes are connected to the capillary tube, with a first one of the at least two electrodes being connected to the capillary tube closer to an inlet of the capillary tube than a second one of the at least two electrodes. The second electrode has an electrical resistance sufficient to cause heating of the electrode during use of the device, thereby minimizing heat loss at the outlet end of the capillary tube.

The invention also provides an aerosol generator that includes a capillary tube having an inlet end, and an outlet end. A first electrode is connected to the capillary tube and a second electrode is connected to the capillary tube, with the first electrode being closer to the inlet end than the second electrode. A voltage is applied between the first and second electrodes to heat a section of the capillary tube between the first and second electrodes, with the capillary tube being hotter at the second electrode than at the first electrode. The second electrode has sufficient electrical resistance to reach a temperature during application of the voltage between the first and second electrodes such that the temperature is hot enough to substantially prevent conduction of heat from the capillary tube to the second electrode.

The invention further provides a method of vaporizing a liquid in a capillary tube having an inlet, an outlet, and a heated section defined between an upstream electrode and a downstream electrode. The downstream electrode has an electrical resistance sufficient to cause heating of the downstream electrode during use of the device, thereby minimizing heat loss at the outlet end of the capillary tube, and both the upstream and downstream electrodes are electrically connected to the capillary tube. The method includes supplying liquid into the capillary tube through the inlet, and applying a voltage across the electrodes to generate heat in the heated section. The voltage also generates sufficient heat in the downstream electrode to substantially eliminate any significant temperature gradient between the downstream electrode and the capillary tube at the connection between the downstream electrode and the capillary tube.

BRIEF DESCRIPTION OF THE DRAWINGS

The invention of the present application will now be described in more detail with reference to preferred embodiments of the apparatus and method, given only by way of example, and with reference to the accompanying drawings, in which.

DESCRIPTION OF THE PREFERRED EMBODIMENTS

The invention provides a fluid vaporizing device useful for applications including aerosol generation. The device includes a heater/capillary tube having a flow passage with an inlet, an outlet, and at least two electrodes connected to electrically conductive material of the capillary tube at spaced points along the flow passage between the inlet and the outlet. The flow passage is defined by the interior of the capillary tube, which is preferably made from an electrically conductive material such as stainless steel. A section of the capillary tube between the inlet and a first electrode constitutes a feed section, and a section of the capillary tube between the first and second electrodes constitutes a heated section. A voltage applied between the first and second electrodes generates heat in the heated section based on the resistivity of the stainless steel or other electrically conductive material forming the capillary tube, as well as the cross-sectional area and the length of the heated section.

An aerosol can be formed from a liquid using a heater capillary by supplying liquid under pressure to an upstream end of the flow passage at an inlet to the capillary tube, and passing the liquid through the feed section of the capillary tube into the heated section. When the liquid is flowing through the capillary tube, as it enters the heated section, initially the liquid is heated and heat conduction to the fluid from the heated capillary tube is high. As the heated liquid continues to move along the heated section toward the outlet or tip of the capillary tube, the liquid is converted to a vapor. The coefficient of heat transfer from the wall of the heated capillary tube to the vapor is low. As a result, the wall temperature of the capillary tube in the heated section toward the outlet or tip of the capillary tube increases relative to the upstream portion of the tube. However, if the electrode at the tip of the capillary acts as a heat sink, it may be more difficult to maintain the temperature of the vapor exiting from the tip of the capillary tube at the optimum temperature for producing aerosol having the desired aerosol droplet size.

In order to improve the temperature profile of the capillary tube, the electrode at the downstream or exit end of the heated section according to an embodiment of the present invention is provided with a predetermined electrical resistance which causes the electrode to heat up when voltage is applied, and thereby minimize a temperature gradient between the wall of the capillary tube at the downstream end of the heated section and the downstream electrode. The electrical resistivity, cross-sectional area, and length of the electrode at the downstream end of the heated section can be selected to minimize or eliminate the above-mentioned temperature gradient and prevent the downstream electrode from acting as a heat sink, thereby minimizing loss of heat from the downstream end of the heated section. The electrical resistivity of the downstream electrode that achieves the optimum balancing of heat transfer along the capillary tube may be selected to accommodate changes in the thermal profile as a function of the desired flow rate of fluid and/or vapor through the tube.

By minimizing the loss of heat from the downstream end of the heated section, a desired exit temperature for the vapor leaving the heated section can be maintained without having to heat the fluid flowing through the intermediate portions of the heated section to as high a temperature as in the case where the downstream electrode conducts heat away from the tip of the capillary tube. This feature provides a significant advantage over a heated capillary tube where the downstream electrode has a very low electrical resistance. In a heated capillary tube where the downstream electrode has a very low electrical resistance, the electrode will have a temperature significantly lower than the temperature at the wall of the downstream end of the heated section of the capillary tube and can act as a heat sink. If the downstream electrode acts as a heat sink, more heat must be input to the liquid passing through the capillary tube in order to maintain a desired temperature for the vapor exiting from the capillary tube. The resulting high temperatures of the fluid passing through the capillary tube can possibly lead to thermal degradation of the fluid especially in the case of vaporizing medicated fluids.

FIG. 1 shows an example of a fluid vaporizing device in the form of an aerosol generator 10 in accordance with one embodiment of the invention. As shown, the aerosol generator 10 includes a source 12 of fluid, a valve 14, a heated capillary passage 20, a mouthpiece 18, an optional sensor 15 and a controller 16. The controller 16 includes suitable electrical connections and ancillary equipment such as a battery which cooperates with the controller for operating the valve 14, the sensor 15 and supplying electricity to heat the capillary passage 20. In operation, the valve 14 can be opened to allow a desired volume of fluid from the source 12 to enter the passage 20, prior to or subsequent to detection by the sensor 15 of vacuum pressure applied to the mouthpiece 18 by a user attempting to inhale aerosol from the aerosol generator 10. As fluid is supplied to the passage 20, the controller 16 controls the amount of power provided to heat the fluid to a suitable temperature for volatilizing the fluid therein. The volatilized fluid exits the outlet of the passage 20, and the volatilized fluid forms an aerosol which can be inhaled by a user drawing upon the mouthpiece 18.

The aerosol generator shown in FIG. 1 can be modified to utilize different fluid supply arrangements. For instance, the fluid source can comprise a delivery valve which delivers a predetermined volume of fluid to the passage 20 and/or the passage 20 can include a chamber of predetermined size to accommodate a predetermined volume of fluid to be volatilized during an inhalation cycle. In the case where the passage includes a chamber to accommodate a volume of fluid, the device can include a valve or valves downstream of the chamber for preventing flow of the fluid beyond the chamber during filling thereof. If desired, the chamber can include a preheater arranged to heat fluid in the chamber such that a vapor bubble expands and drives the remaining liquid from the chamber into the passage 20. Details of such a preheater arrangement can be found in commonly owned U.S. application Ser. No. 09/742,395 filed on Dec. 22, 2000, the disclosure of which is hereby incorporated by reference. If desired, the valve(s) could be omitted and the fluid source 12 can include a delivery arrangement such as a syringe pump, which supplies a predetermined volume of fluid to the chamber or directly to the passage 20. The heater can be the walls of the capillary tube defining passage 20, arranged to volatilize the liquid in passage 20. The entire wall of the capillary tube defining passage 20 can be made from an electrically conductive material such as stainless steel, so that as a voltage is applied to the tube, the tube is heated by the flow of electric current through the tube. As an alternative, the tube could be made from a non-conductive or semi-conductive material, such as glass or silicon, the tube including a heater formed from a resistance heating material such as platinum (Pt).

Figure 1:
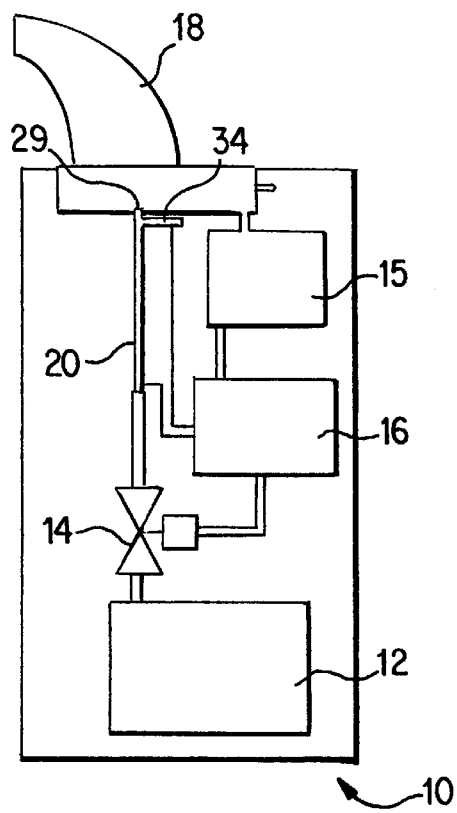
FIG. 1 illustrates a fluid vaporizing device according to an embodiment of the invention.
Figure 2:
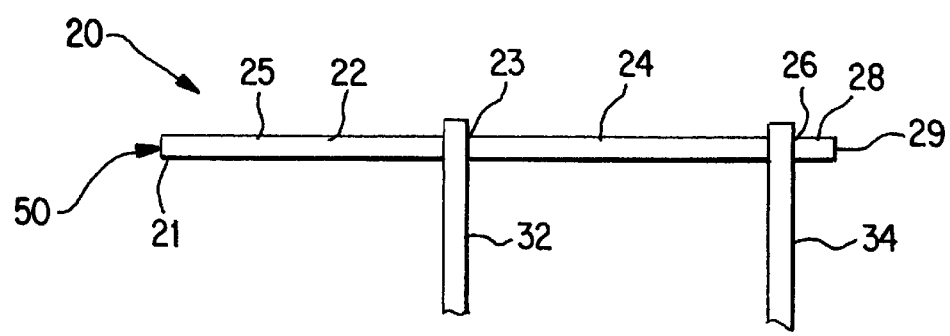
FIG. 2 is a schematic representation of a heated capillary tube according to an embodiment of the invention.

In the case of manual operations, the sensor 15 can be omitted such as in the case where the aerosol generator 10 is operated manually by a mechanical switch, electrical switch or other suitable technique. Although the aerosol generator 10 illustrated in FIG. 1 is useful for medical uses, the principles of the device can also be used in an application for vaporizing a fuel.

According to one aspect of the present invention, a capillary aerosol generator is formed from a tube made entirely of stainless steel or other electrically conductive materials, or a non-conductive or semi-conductive tube incorporating a heater formed from an electrically conductive material such as platinum (Pt). Two electrodes are connected at spaced positions along the length of the tube, with a feed section being defined between the inlet end of the tube and the upstream electrode, a heated section being defined between the two electrodes, and a tip section between the downstream electrode and the exit end of the tube. A voltage applied between the two electrodes generates heat in the heated section based on the resistivity of the stainless steel or other material making up the tube or heater, and other parameters such as the cross-sectional area and length of the heated section. Fluid can be supplied to the aerosol generator, preferably at a substantially constant pressure and/or in a predetermined volume of fluid, from a fluid source upstream of the tube. The fluid passes through the feed section of the capillary tube between the inlet and the first electrode. As the fluid flows through the capillary tube into the heated section between the first and second electrodes, the fluid is heated and converted to a vapor. The vapor passes from the heated section of the capillary tube to the tip of the capillary tube and exits from the outlet end of the capillary tube. If the volatilized fluid enters ambient air from the tip of the capillary tube, the volatilized fluid condenses into small droplets, thereby forming an aerosol preferably having a size of less than 10 $\mu$m, preferably 1 to 2 $\mu$m. However, the fluid can comprise a liquid fuel which is vaporized in the tube and passed into a hot chamber in which the vapor does not condense into an aerosol. In a preferred embodiment, the capillary tube has an inner diameter of 0.1 to 0.5 mm, more preferably 0.2 to 0.4 mm, and the heated zone has a length of 5 to 40 mm, more preferably 10 to 25 mm.

As fluid initially enters the heated section of the capillary tube, conduction of heat to the fluid is high since there is a relatively high heat transfer coefficient between the fluid and the wall of the tube. As the heated fluid continues to move downstream along the heated section, the fluid is converted to a vapor. The heat transfer coefficient between the wall and the vapor is low. With less heat being conducted to the vapor, the wall temperature of the capillary tube increases in the area containing vapor.

The wall temperature at the downstream end of the heated section is preferably maintained at a desired temperature by providing a downstream electrode which minimizes heat loss. For example, heat can be prevented from being conducted away from the tube by the downstream electrode in the case where the downstream electrode is provided with a high enough electrical resistance to generate sufficient heat to maintain the downstream end of the capillary tube wall at a desired temperature, thereby minimizing a temperature gradient and hence the driving force for heat conduction.

According to a first exemplary embodiment, a capillary aerosol generator 20 includes a capillary tube 25 having an inlet end 21, an outlet end 29, and at least one upstream electrode 32 and one downstream electrode 34 connected to the capillary tube at points 23 and 26, respectively, by known means such as brazing or welding. The electrodes 32, 34 divide the capillary tube into an upstream feed section 22 between the inlet 21 and the first electrode 32, an intermediate heated section 24 between the first electrode 32 and the second electrode 34, and a downstream tip 28 defined between the second electrode 34 and the outlet end 29 of the capillary tube.

Fluid from a fluid source 50 is provided to the heated capillary tube through inlet end 21, e.g., fluid can be supplied in the form of a pressurized liquid. As the liquid passes through the capillary tube from the feed section 22 into the heated section 24, heat generated by passing an electrical current between the electrodes 32 and 34 is conducted to the liquid passing through the heated section. As the liquid continues downstream through the heated section, the liquid is converted to vapor by the input of heat. The heat transfer coefficient between the wall and the vapor is less than the heat transfer coefficient between the wall and the liquid. Therefore, the downstream portion of the capillary tube closer to the downstream electrode 34 is heated to a higher temperature than a portion of the tube closer to the upstream electrode 32. In order to prevent the mass of the downstream electrode 34 from acting as a heat sink that would conduct heat away from the capillary tube, the downstream electrode 34 is made from an electrically resistive material that provides a desired downstream electrode temperature during the application of electrical current through the electrodes 32, 34. The electrical resistivity of electrode 34, along with other parameters including its cross-sectional area and length can be chosen in order to minimize any heat sink effect that the electrode 34 may have on the capillary tube. The selection of these parameters can be a function of the desired flow rate of fluid/vapor through the capillary tube. At higher flow rates, more heat must be input to the heated section to maintain the desired exit temperatures for the vapor. Higher power input is required to maintain the preferred temperature profile as the flow rate is increased. Higher power requires a higher current in accordance with the relationship that power equals $I^2R$. Higher electrical current is needed in the fluid channel because of the higher heat dissipation rate at higher flow rates. However, unless the resistivity of the downstream electrode is changed, the higher power input may result in too much heat being generated at the downstream electrode. Therefore, at higher flow rates through the capillary tube, the resistance of the downstream electrode may actually be reduced while achieving the desired temperature to avoid any temperature gradient between the downstream electrode and the downstream end of the capillary tube. Accordingly, the temperature profile of the capillary tube along the heated section can be controlled and excessive heating of the fluid/vapor passing through the heated section can be avoided.

Figure 3:
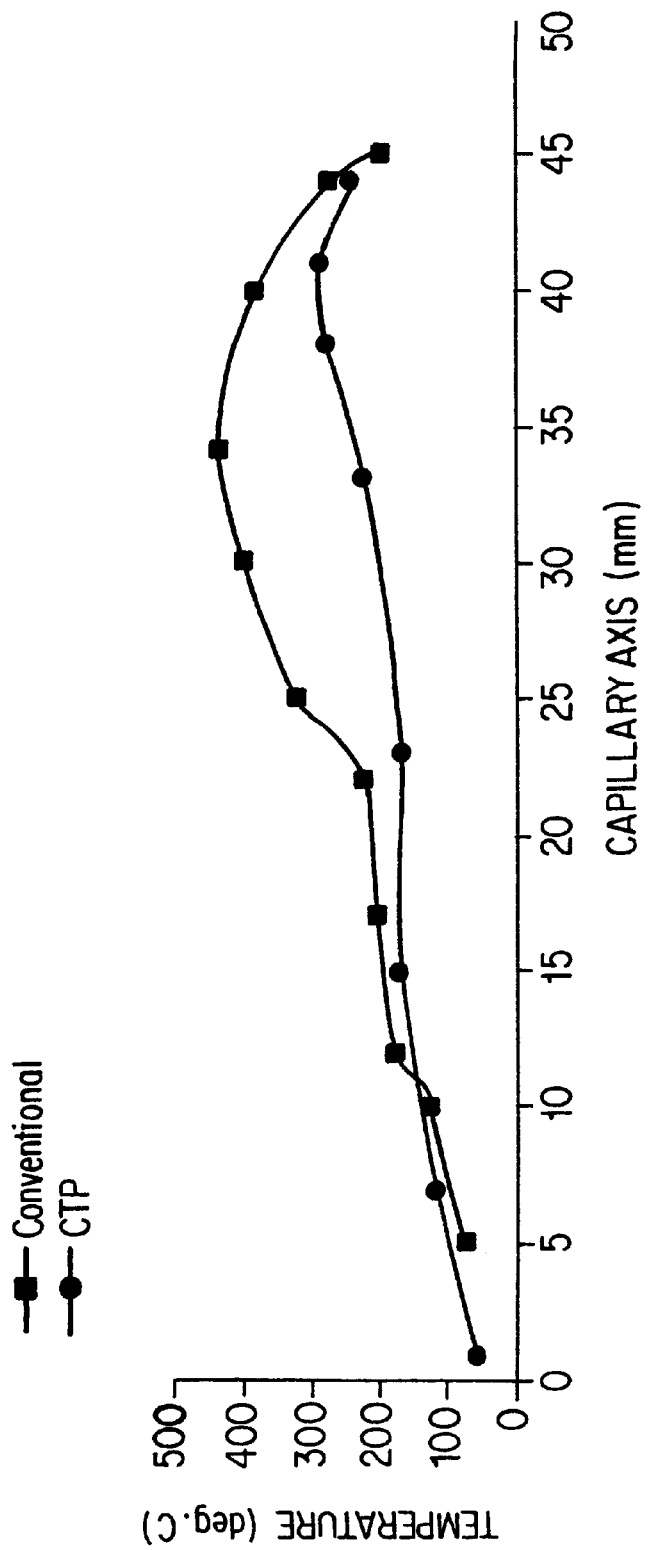
FIG. 3 illustrates wall temperature profiles for a comparative heated capillary tube and a heated capillary tube according to the present invention.

FIG. 3 illustrates a comparison of wall temperature profiles in an aerosol generator having electrodes of the same highly conductive material, and in the controlled temperature profile (CTP) aerosol generator according to the invention. The controlled temperature profile of the capillary tube along the heated section enables maintenance of a desired exit temperature for vapor leaving from the tip of the tube without overheating the fluid/vapor upstream thereof.

Another advantage that results from controlling the temperature profile along the capillary tube in medical applications is that the tip of the tube can more easily be maintained at a high enough temperature to optimize the formation of an aerosol with particles in the preferred range of less than 10 microns, preferably less than 5 microns in diameter, at which the particles in the form of droplets or solid particles are more effectively passed to the lungs of a user for delivery of medicaments.

From the foregoing, it will be apparent that the electrical resistance, cross-sectional area and length of the downstream electrode can be varied to achieve the desired temperature profile along the heated section of the capillary tube, with the resulting operational temperature of the downstream electrode balancing the temperature of the capillary tube near the tip, and thereby substantially eliminating any heat sink effect by the downstream electrode. For instance, the downstream electrode can comprise a 5 to 7 mm section of stainless steel tubing attached between the capillary tube and a low resistance wire completing the circuit to the power supply. The electrodes can be connected to the capillary tube using conventional methods that may include, but are not limited to, brazing, welding, and soldering, or the electrodes could be formed integrally with the capillary tube. In implementing the capillary heater in an inhaler, the capillary tube is preferably insulated and/or isolated from ambient air and the vapor emitted from the capillary tube. For example, an insulating material or a metal foil, such as stainless steel foil, could be used to support the capillary tip within a mouthpiece such that the vapor exiting the capillary tube does not contact the outer surface of the capillary tube upstream of the metal foil.

While this invention has been illustrated and described in accordance with a preferred embodiment, it is recognized that variations and changes may be made therein without departing from the invention as set forth in the claims.

What is claimed is:

1. A fluid vaporizing device comprising:
   a capillary tube made from an electrically conductive material, said capillary tube providing a passageway for a fluid;
   at least two electrodes connected to said capillary tube, a first one of said at least two electrodes being connected to said capillary tube closer to an inlet of said capillary tube than a second one of said at least two electrodes, electrical power being provided to said capillary tube through said at least two electrodes to heat said capillary tube;
   said second electrode having an electrical resistance which causes heating of said second electrode during the application of electrical power to approximately a same temperature as said capillary tube at a point of connection between said second electrode and said capillary tube.

2. The fluid vaporizing device according to claim 1, wherein said capillary tube includes a feed section between said inlet and said first electrode, a heated section between said first and second electrodes, and a tip between said second electrode and an outlet of said capillary tube.

3. The fluid vaporizing device according to claim 2, wherein said second electrode has a temperature sufficiently high to prevent the conduction of heat from said capillary tube to said second electrode.

4. The fluid vaporizing device according to claim 1, wherein the fluid vaporizing device comprises an inhaler having a mouthpiece, the capillary tube having an outlet which directs vaporized fluid into the mouthpiece.

5. The fluid vaporizing device according to claim 1, wherein the device comprises an inhaler having a controller, a valve and a sensor, the sensor detecting a delivery condition corresponding to delivery of a predetermined volume of aerosol, the controller being programmed to open the valve so as to deliver liquid to the capillary tube when the delivery condition is sensed by the sensor and to pass electrical current through the capillary tube to volatilize liquid therein.

6. An aerosol generator, comprising:
   a capillary tube having an inlet end, and an outlet end;
   a first electrode connected to said capillary tube and a second electrode connected to said capillary tube, said first electrode being closer to said inlet end than said second electrode;
   a voltage being applied between said first and second electrodes and heating a section of said capillary tube between said first and second electrodes, with said second electrode being at least as hot as a downstream end of the heated section of the capillary tube; and
   said second electrode having an electrical resistance which causes heating of the second electrode during application of said voltage between said first and second electrodes, such that a temperature gradient between the capillary tube and second electrode at the point of connection is minimized.

7. The aerosol generator according to claim 6, wherein a fluid passing through said capillary tube is in substantially a liquid phase in the vicinity of said first electrode, and is in substantially a vapor phase in the vicinity of said second electrode.

8. The aerosol generator according to claim 7, wherein said capillary tube has a higher temperature in the vicinity of said second electrode than in the vicinity of said first electrode as a result of a lower heat transfer coefficient between said vapor phase of said fluid and said capillary tube than the heat transfer coefficient between said liquid phase of said fluid and said capillary tube.

9. A method of vaporizing a fluid in a capillary tube having an inlet, an outlet, and a heated section defined between an upstream electrode and a downstream electrode, and both said upstream and downstream electrodes being electrically connected to said capillary tube, said method comprising:
   supplying liquid into said capillary tube through said inlet; and
   applying a voltage across said electrodes to generate heat in said heated section, said voltage also generating enough heat in said downstream electrode to minimize a temperature gradient between said downstream electrode and said capillary tube at a connection between the downstream electrode and the capillary tube.

10. The method according to claim 9, wherein the electrical resistivity of the downstream electrode is predetermined as a function of the desired flow rate of the liquid being passed through said capillary tube.

11. The method according to claim 10, wherein said liquid is converted to a vapor in said heated section.

12. The method according to claim 10, wherein the capillary tube is part of an inhaler which includes a controller, a valve and a sensor, the method including sensing a delivery condition with the sensor, sending a signal to the controller corresponding to the delivery condition, opening the valve for delivery of a predetermined volume of the liquid to the capillary tube, supplying power to the capillary tube, and closing the valve after the predetermined volume of liquid has been delivered to the capillary tube.

13. The method according to claim 10, wherein the outlet of the capillary tube is in close proximity to the downstream electrode and the vapor exiting the outlet condenses in ambient air and forms an aerosol.

14. The method according to claim 10, wherein the liquid comprises a solution of medicated material and the vapor exiting the capillary tube forms an aerosol containing medicated material.

* * * * *